United States Patent
Stoyanov et al.

(10) Patent No.: US 11,615,884 B2
(45) Date of Patent: Mar. 28, 2023

(54) TECHNIQUES FOR VIRTUALIZED TOOL INTERACTION

(71) Applicant: Digital Surgery Limited, London (GB)

(72) Inventors: Danail Stoyanov, London (GB); Petros Giataganas, London (GB); Piyamate Wisanuvej, London (GB); Paul Riordan, London (GB); Imanol Luengo Muntion, London (GB); Jean Nehme, London (GB)

(73) Assignee: DIGITAL SURGERY LIMITED, London (GB)

( * ) Notice: Subject to any disclaimer, the term of this patent is extended or adjusted under 35 U.S.C. 154(b) by 842 days.

(21) Appl. No.: 16/294,576

(22) Filed: Mar. 6, 2019

(65) Prior Publication Data

US 2019/0279524 A1 Sep. 12, 2019

Related U.S. Application Data

(60) Provisional application No. 62/639,348, filed on Mar. 6, 2018.

(51) Int. Cl.
*G06F 3/01* (2006.01)
*G09B 9/00* (2006.01)
(Continued)

(52) U.S. Cl.
CPC .............. *G16H 40/63* (2018.01); *G06F 3/014* (2013.01); *G06F 3/017* (2013.01); *G06F 16/22* (2019.01);
(Continued)

(58) Field of Classification Search
CPC ........ G16H 40/63; G16H 10/60; G16H 50/70; G16H 30/40; G06F 16/22; G06F 3/01;
(Continued)

(56) References Cited

U.S. PATENT DOCUMENTS 6,132,368 A 10/2000 Cooper
6,206,903 B1 3/2001 Ramans
(Continued)

OTHER PUBLICATIONS

CyberGlove Systems, CyberGlove II Wireless Data Glove: User Guide, 2009. (Year: 2009).*
(Continued)

*Primary Examiner* — Jay Trent Liddle
*Assistant Examiner* — Alyssa N Brandley
(74) *Attorney, Agent, or Firm* — Cantor Colburn LLP

(57) ABSTRACT

A computer implemented method is provided for a virtual training system. A virtual surgical simulation associated with a type of surgical procedure is accessed. Image data associated with a controller and a workspace is received. Controller data corresponding to a controller interaction is received. A first interaction of the controller within the workspace based on at least one of the image data and the controller data is determined. Using the set of one or more transformation rules, the first interaction of the controller is transformed to a manipulation of a virtualized surgical tool in the virtual surgical simulation. A representation is output of the manipulation of the virtualized surgical tool.

20 Claims, 11 Drawing Sheets

(51) Int. Cl.
  *G09B 23/28* (2006.01)
  *G16H 40/63* (2018.01)
  *G16H 50/70* (2018.01)
  *G06F 16/22* (2019.01)
  *G06N 5/02* (2023.01)
  *G16H 10/60* (2018.01)
  *G16H 30/40* (2018.01)
  *G06V 20/40* (2022.01)

(52) U.S. Cl.
  CPC ............. *G06N 5/02* (2013.01); *G06V 20/41* (2022.01); *G06V 20/47* (2022.01); *G09B 9/00* (2013.01); *G09B 23/28* (2013.01); *G16H 10/60* (2018.01); *G16H 30/40* (2018.01); *G16H 50/70* (2018.01); *G06V 2201/10* (2022.01)

(58) Field of Classification Search
  CPC ........... G06F 3/014; G06F 3/017; G06N 5/02; G09B 9/00; G09B 23/28; G06V 2201/10; G06V 20/41; G06V 20/47
  USPC ......................................................... 434/262
  See application file for complete search history.

(56) References Cited

U.S. PATENT DOCUMENTS

| | | | |
|---|---|---|---|
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll et al. | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,084,884 B1 * | 8/2006 | Nelson ............... G06F 3/014 | |
| | | | 345/156 |
| 7,118,582 B1 | 10/2006 | Wang et al. | |
| 7,121,832 B2 | 10/2006 | Hsieh et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco et al. | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez et al. | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |

(56) References Cited

U.S. PATENT DOCUMENTS

| | | |
|---|---|---|
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,355,574 B2 * | 5/2016 | Jian .................. G06T 19/20 |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,788,907 B1 | 10/2017 | Alvi et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,002,286 B1 | 6/2018 | Prabhu et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,147,052 B1 | 12/2018 | Lendvay et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |

(56) References Cited

U.S. PATENT DOCUMENTS

| | | |
|---|---|---|
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 2006/0084050 A1* | 4/2006 | Haluck ............... G09B 23/28 434/262 |
| 2007/0136218 A1 | 6/2007 | Bauer et al. |
| 2008/0187896 A1 | 8/2008 | Savitsky |
| 2009/0177452 A1* | 7/2009 | Ullrich ............... G06F 3/014 703/11 |
| 2010/0167249 A1* | 7/2010 | Ryan ............... G09B 23/285 434/267 |
| 2010/0241998 A1* | 9/2010 | Latta ............... G06F 3/011 715/862 |
| 2010/0248200 A1 | 9/2010 | Ladak et al. |
| 2013/0230837 A1* | 9/2013 | Meglan ............... G09B 23/28 434/262 |
| 2013/0295540 A1* | 11/2013 | Kesavadas ............ G09B 23/28 434/262 |
| 2014/0272866 A1* | 9/2014 | Kim ............... G09B 23/28 434/262 |
| 2015/0248167 A1* | 9/2015 | Turbell ............... G06F 3/0481 715/754 |
| 2016/0133158 A1* | 5/2016 | Sui ............... G09B 23/283 434/262 |
| 2016/0182877 A1* | 6/2016 | Deluca ............... G06F 3/011 348/54 |
| 2016/0378176 A1* | 12/2016 | Shiu ............... G06F 3/011 345/633 |
| 2017/0116873 A1 | 4/2017 | Lendvay et al. |
| 2017/0140671 A1 | 5/2017 | Wystan et al. |
| 2017/0220816 A1 | 8/2017 | Matusek et al. |
| 2017/0289623 A1 | 10/2017 | Bailey et al. |
| 2017/0312031 A1* | 11/2017 | Amanatullah ......... A61B 34/10 |
| 2018/0005546 A1* | 1/2018 | Vazquez ............... G09B 23/285 |
| 2018/0300897 A1* | 10/2018 | Woods ............... G06F 3/0484 |
| 2018/0325618 A1* | 11/2018 | Justin ............... A61B 34/20 |
| 2019/0090954 A1 | 3/2019 | Kotian |
| 2019/0133689 A1* | 5/2019 | Johnson ............... A61B 34/10 |
| 2019/0180083 A1 | 6/2019 | Gupta et al. |
| 2019/0279765 A1 | 9/2019 | Giataganas et al. |
| 2020/0118677 A1 | 4/2020 | Giataganas et al. |

OTHER PUBLICATIONS

Webpage: "https://usens.com/fingo", uSens, Inc., page downloaded Aug. 6, 2019.

Webpage: "https://www.captoglove.com", captoglove.us, page downloaded Aug. 6, 2019.

Webpage: "https://uk.3dsystems.com/scanners-haptics#haptics-devices", 3D Systems, Inc., page downloaded Aug. 6, 2019.

Webpage: "http://uk.3dsystems.com/learning-center/case-studies/doctors-practicing-computers-not-patients", 3D Systems, Inc., page downloaded Aug. 6, 2019.

Webpage: "https://simbionix.com/simulators/robotix-mentor/", 3D Systems, Inc. page downloaded Aug. 6, 2019.

Webpage: "https://mimicsimulation.com/flexvr/", Mimic Technologies, Inc., Downloaded Aug. 6, 2019.

Extened European Search Report dated Jul. 30, 2019 in related foreign application No. EP 19161135.9, 10 pages.

\* cited by examiner

TECHNIQUES FOR VIRTUALIZED TOOL INTERACTION

CROSS-REFERENCE TO RELATED APPLICATIONS

This application claims the benefit of and the priority to U.S. Provisional Application No. 62/639,348, filed on Mar. 6, 2018, which is hereby incorporated by reference in its entirety for all purposes.

FIELD

The present disclosure generally relates to a portable surgical simulation system. More particularly, the present disclosure relates to a portable surgical simulation system that virtualizes surgical tools (e.g., graspers, diathermy, scissors, etc.) and facilitates simulation of virtualized surgical tools in various surgical procedures in a three-dimensional environment.

BACKGROUND

Surgeons are currently trained with traditional hands on methods of observation and apprenticeship. These traditional methods of training require constant supervision by highly skilled instructors, thus limiting the number of persons who can be competently trained to perform procedures in a specified amount of time. For example, surgical actions such as piercing and incision are very common operations in a surgery that are basic skills for any surgeon. For surgery, such as intervention of tumor, fetal diagnosis, radio frequency tumor ablation, local anesthesia, percutaneous catheterization and endoscopic surgery, a high of level of skill is required because of the difficulty of the operation. Often, extensive training is required to master these skills. For example, a surgeon may need to practice on dozens of patients in order to develop these skills.

However, since many of the surgeries are highly risky, it is not feasible to master these skills through practice on patients. In recent years, various visual surgical simulations systems have been proposed to permit input of a desired manipulation and to display a simulation result on a display. However, there are considerable visual errors and inaccuracies when tracking movement in these systems. In addition, since the manipulation accuracy is limited, and since the input information cannot adequately match the manipulation in an actual operation, the simulation result is expectedly low and unreliable.

BRIEF SUMMARY

In some embodiments, a computer-implemented method is provided. A virtual surgical simulation associated with a type of surgical procedure is accessed. The virtual surgical simulation includes a set of one or more transformation rules that correspond to a model for a virtualized surgical tool to be represented in the virtual surgical simulation. Image data is received associated with a controller and a workspace. Controller data is received corresponding to a controller interaction. A first interaction of the controller is determined within the workspace based on at least one of the image data and the controller data. In some cases, the image data is generated based on projection of a structured light field. In some cases, the method includes projecting a light pattern that is present in the image data. In some cases, the method includes detecting a distortion in the light pattern; determining a shape of an object in the image data based on the distortion in the light pattern; and determining the shape of the object is the controller. In some cases, receiving image data further comprises: emitting infrared light; and receiving, by an infrared stereo camera, the image data. In some cases, determining the virtual surgical tool associated with the controller further comprises receiving a tool model selected by a user. In some cases, the controller data is associated with seven degrees of freedom. In some cases, the controller is tethered to a mobile device. In some cases, determining the manipulation of the virtual surgical tool further comprises determining a trajectory associated with the controller. In some cases, the method further comprises detecting one or more markers associated with the controller from the image data. In some cases, detecting one or more markers associated with the controller from the image data comprises: determining three or more markers are present in the image data; and determining, using the three or more markers, a full pose of a rigid body in a workspace coordinate system corresponding to the controller. In some cases, the virtual surgical simulation further comprises a 3D environment. In some cases, the virtual surgical simulation is output to a display on a mobile device. In some cases, the virtual surgical simulation is output to an augmented reality headset. In some cases, the virtual surgical simulation is output to a virtual reality headset. In some cases, the method further comprises further comprising transmitting data to the controller via at least one of a Bluetooth™ connection and a Wi-Fi connection. In some cases, the controller data further comprises pressure data associated with force sensors on the controller.

In some embodiments, a computer-implemented method is provided. A virtual surgical simulation associated with a type of surgical procedure is accessed. The virtual surgical simulation includes a set of one or more transformation rules that correspond to a model for a virtualized surgical tool to be represented in the virtual surgical simulation. An interaction with a controller is detected. The interaction with the controller can be detected from at least one of image data associated the virtual surgical simulation and data transmitted by the controller. The interaction with the controller is transformed to a manipulation of the virtualized surgical tool. The virtualized surgical tool in the virtual surgical simulation is updated using the manipulation of the virtualized surgical tool. Based on the manipulation, a virtual interaction associated with the virtualized surgical tool interacting with a virtualized anatomical structure in the virtual surgical simulation is determined. The interaction score is transmitted to a user interface. In some cases, the interaction score comprises at least one of a dexterity measurement, an economy of movement measurement, and a motion related measurement. In some cases, the method further comprises generating a command that causes the controller to provide feedback to a user, wherein the feedback includes at least one of kinesthetic, tactile, visual, and auditory feedback.

In some cases, the feedback is associated with a target biological effect in the virtual surgical simulation environment.

In some embodiments, a computer-implemented method is provided. A virtual surgical simulation associated with a type of surgical procedure is accessed. The virtual surgical simulation includes one or more tool profiles, each tool profile including a set of one or more transformation rules that correspond to a model for a virtualized surgical tool to be represented in the virtual surgical simulation. From the one or more tool profiles, a first tool profile is identified that corresponds to a first interaction with a controller. Using the first tool profile, the first interaction with the controller is transformed to a first manipulation of a first virtualized surgical tool. The first manipulation is output to a user interface. From the one or more tool profiles, a second tool profile is identified that corresponds to a second interaction with the controller. Using the second tool profile, the second interaction with the controller is transformed to a second manipulation of a second virtualized surgical tool. The second manipulation is output to the user interface. In some cases, the method further comprises determining feedback based on the virtualized surgical tool, the controller, the one or more tool profiles, and the virtual surgical simulation. In some cases, each tool profile of the one or more tool profiles comprises at least one or more of a marker configuration, dimensions, shapes, axes of rotation, tensions, and movement constraints. In some cases, the method further comprises identifying a marker configuration corresponding to at least one of the first virtualized surgical tool and the second virtualized surgical tool. In some cases, the method further comprises accessing a user profile with a hand profile including hand shape, hand size, movement characteristics, and rest-state characteristics. In some cases, the method further comprises generating a command that causes the controller to provide feedback based on at least one of the tool profiles and a user profile. In some cases, the method further comprises generating a tool selection recommendation based on at least one of the first interaction and the second interaction.

In some embodiments, a computer-implemented method is provided. A virtual surgical simulation associated with a type of surgical procedure is accessed. The type of surgical procedure is associated with a map representing an ordered progression of the type of surgical procedure using a plurality of interconnected nodes, each node representing a procedural state. The virtual surgical simulation includes a model for a virtualized surgical tool to be represented in the virtual surgical simulation. Controller data is received. The controller data represents an interaction with a controller. The controller data is transformed to a manipulation of the virtualized surgical tool in the virtual surgical simulation. The manipulation of the virtualized surgical tool is determined causing a transition to a new procedural state associated with a new node in the map. The new node is interconnected with a current node. One or more virtualized anatomical structures is updated in the virtual surgical simulation based on the new procedural state. In some cases, the method further comprises generating a chance variable; determining the new node of the virtual surgical simulation based on the chance variable and the manipulation; and updating the virtual surgical simulation based on the new node. In some cases, the method further comprises accessing a first node with a first weighted probability and a second node with a second weighted probability; determining a target manipulation associated with the first node and the second node; determining a target score using the target manipulation and the manipulation associated with the virtualized surgical tool; and selecting the new node based on the first weighted probability, the second weighed probability, and the target. In some cases, the method further comprises providing a user interface including a representation of the map indicating a progression from a current node to one or more next nodes, wherein each node of the one or more next nodes is associated with a probability. In some cases, the method further comprises detecting a next node from the one or more next nodes selected by a user.

In some embodiments, a computer-implemented method is provided. A virtual surgical simulation associated with a type of surgical procedure is accessed. The virtual surgical simulation includes a set of one or more default transformation rules that correspond to a model for a virtualized surgical tool to be represented in the virtual surgical simulation. Image data is received. An object is detected in the image data. The object is determined as a hand of a user. Based on the image data, one or more hand features associated with the object are identified. A user specific set of one or more transformation rules associated with the one or more hand features is generated. In some cases, the method further comprises determining a user profile associated with the hand of the user; associating the hand features with the user profile; and storing the user profile. In some cases, the method further comprises transmitting one or more calibration instructions to a user interface.

In some embodiments, a computer-program product is provided that is tangibly embodied in a non-transitory machine-readable storage medium. The computer-program product can include instructions configured to cause one or more data processors to perform operations of part or all of one or more methods disclosed herein.

In some embodiments, a system is provided that includes one or more data processors and a non-transitory computer readable storage medium containing instructions which, when executed on the one or more data processors, cause the one or more data processors to perform operations of part or all of one or more methods disclosed herein.

The following detailed description together with the accompanying drawings will provide a better understanding of the nature and advantages of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood in view of the following non-limiting figures, in which.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

The structures and technologies described herein may function in combination to provide basic dexterity training for users training to use a robotic surgery system. Embodiments described herein provide a portable interaction system compatible with mobile devices. In some embodiments, a physical controller is provided that can be moved along one or more dimensions. For example, the entire controller can be moved in three-dimensional space and/or rotated (e.g., to correspond to up to six degrees of freedom, and/or the controller can have one or more additional degrees of freedom (e.g., due to an existence of one or more joints). The movement can be tracked using data received from (for example) a camera system that includes one or more cameras that can record an interaction by a user with the controller, one or more sensors integrated into the controller, and/or one or more external sensors.

The tracked data can be received at a computer system (e.g., which may include or be independent from the camera system), which can access a profile for a surgical tool to be simulated (e.g., a grasper, diathermy, pair of scissors, etc.). The profile can include one or more transformation data structures that indicate how the tracked data is to be transformed to generate virtualized tool-movement data, simulated surgical actions and/or simulated surgical result(s) of the actions. A result of the transformation can be presented as a visual stimulus (e.g., reflecting a simulated movement of a virtualized tool, a simulated surgical action and/or a simulated surgical result) that can be presented at a display of the computer system. In some instances, a result of the transformation can indicate an extent to which and/or whether movement detected movement corresponds with a target movement. The result can be indicated on a display and/or communicated to the controller, which can provide haptic feedback (e.g., indicating a lack of correspondence).

Figure 1:
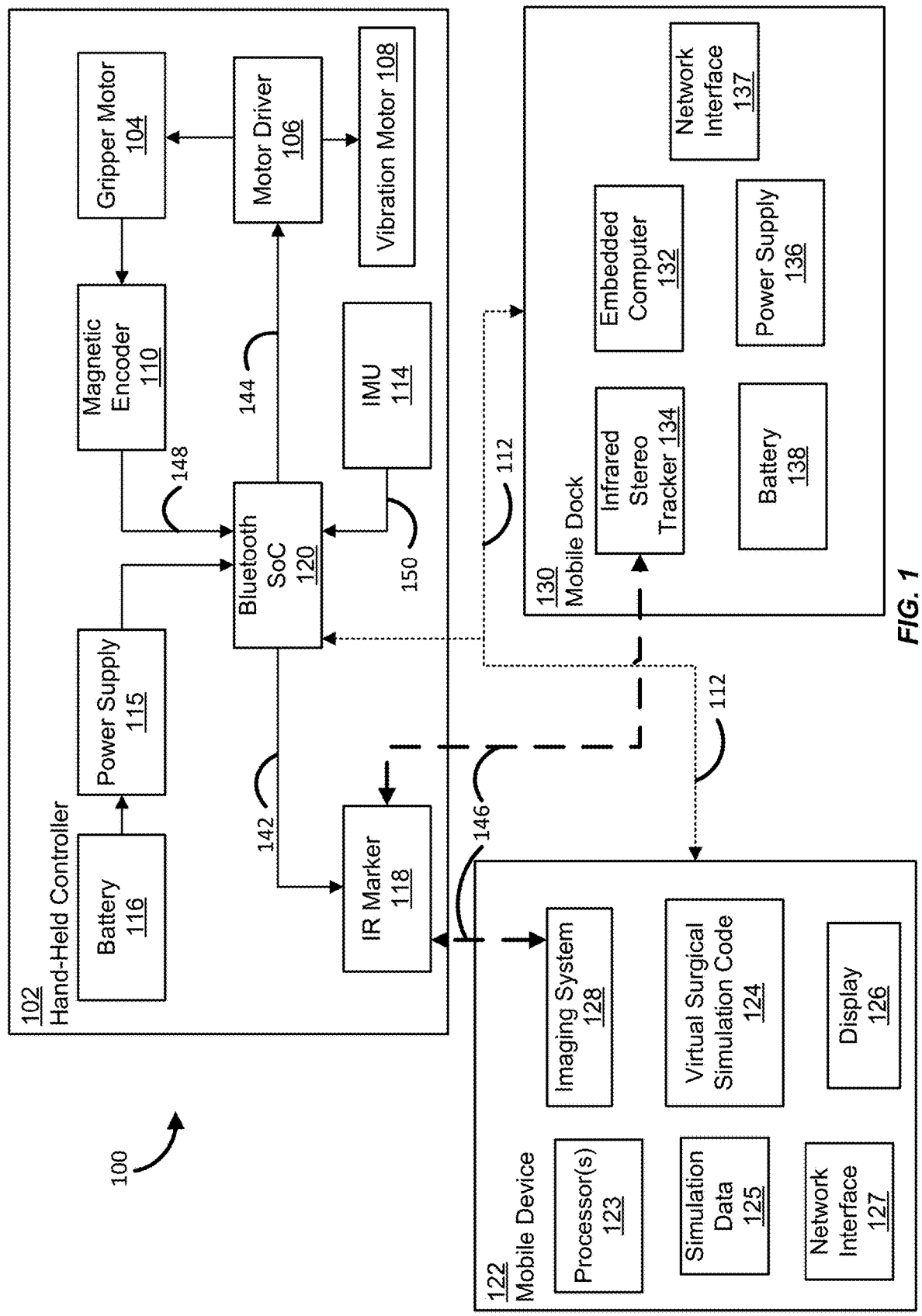
FIG. 1 shows a block diagram of a portable interaction system 100 in accordance with some embodiments of the invention.

FIG. 1 shows a block diagram of a portable interaction system 100. The portable interaction 100 can be implemented using a hand-held controller 102 and a mobile device 122 (e.g., mobile phone, tablet, or other portable computing system) to improve the portability of robotic minimally invasive surgery (RMIS) training systems. In some embodiments, the system can be implemented using the hand-held controller 102, the mobile device 122, and a mobile dock 130 coupled to the mobile device 122.

The controller 102 can include a system on a chip (SoC) 120 to communicate via a communication path 112 with the mobile device 122 and the mobile dock 130. The communication path 112 can be a wired and/or wireless communication path to transmit data and/or power between the controller 102, the mobile device 122, and the mobile dock 130. The data can include controller data corresponding to user interactions with the controller 102, one or more user inputs received by the mobile device 122 and/or the mobile dock 130, and instructions that cause the controller 102 to provide feedback to a user.

In some embodiments, a first pulse-width modulated (PWM) signal 142 can be transmitted to an infrared (IR) marker 118. The first PWM signal 142 can cause the IR marker 118 to emit infrared light 146 that can be detected by the imaging system 128 and/or the infrared stereo tracker 134. The first PWM signal 142 can be a unique signal assigned to the controller 102. The infrared light 146 emitted in response to the first PWM signal 142 can be used by the mobile device 122 and/or the mobile dock 130 to identify the type of controller. In some embodiments, a plurality of IR markers can be used to assist with determining the position and orientation of the controller. In some embodiments, the IR marker 118 can comprise a reflective material configured to reflect infrared light 146 projected by the infrared stereo tracker 134 and/or the imaging system 128.

The mobile device 122 can include one or more processors 123, a network interface 127, the imaging system 128, the virtual surgical simulation code 124, simulation data 125, and a display 126. The virtual surgical simulation code 124 can generate and update a virtual surgical simulation. The virtual surgical simulation can include a variety of blocks, components, modules, objects, data structures, etc. In some embodiments, the virtual surgical simulation code 124 can generate, access, update and/or store the virtual surgical simulation in a storage medium on mobile device 122. The virtual surgical simulation code 124 can access data associated with a surgical procedure. In some embodiments, simulation data 125 can include instructions, stored on a storage medium, that describe one or more surgical training tasks (e.g., pick and place tasks, peg transfers, precision cutting, ligating loops, sutures with an extracorporeal knot, sutures with an intracorporeal knot, or other training tasks) that can be accessed by the virtual surgical simulation code 124. In some embodiments, the virtual surgical simulation code 124 can be implemented in software, hardware, or a combination thereof. The virtual surgical simulation code 124 can include a variety of blocks, components, modules, and/or means to perform various tasks associated with the portable interaction system 100.

The imaging system 128 can include one or more image capture devices and provide image data to the virtual surgical simulation code 124. The imaging system 128 can include one or more elements to output a patterned stimulus to assist with tracking and identifying an object, such as controller 102. The image data captured by the imaging system 128 can include a reflection of the patterned stimulus. The virtual surgical simulation code 124 can process the image data to identify user interactions with the controller 102. The virtual surgical simulation code 124 can transform user interactions with the hand-held controller 102 to a manipulation of a virtualized surgical tool according to a profile for a surgical tool to be simulated. In some embodiments, the profile can be included in the simulation data 125. The profile can include one or more transformation data structures that identify a manipulation of a virtual tool based on image data representing a user interaction with the controller 102. The profile can include a separate set of rules and can indicate target manipulations for the virtual tool according to the training tasks and/or a surgical procedure. The data structures can include attributes that correspond to one or more physical properties of the tool. A representation of the virtualized surgical tool in the virtual surgical simulation can be generated by the virtual surgical simulation code 124. The virtualized surgical simulation code 124 can trigger an output to the display 126 based on a dynamic representation of the virtual tool within a 3D virtual environment and the output can indicate an estimated effect of the manipulation of the virtual tool.

The imaging system 128 and/or the infrared stereo tracker 134 may form a workspace for the portable interaction system 100. The workspace may be a volume in which user interactions with the controller can be accurately captured by the portable interaction system 100. The boundaries of the workspace can be determined by a field of view associated with the imaging system 128 and/or the infrared stereo tracker 134. In some embodiments, the imaging system 128 may capture and convert visual/light data to image data and process the image data to discard image data without the controller 102 in the field of view. The virtual surgical simulation code 124 can receive the image data from the imaging system 128 and process the image data associated with the controller.

In addition to the image data, the portable interaction system 100 can receive controller data corresponding to user interaction with the controller. The user interaction with the controller can be measured by one or more sensors embedded in the controller 102 (e.g., optical sensors; strain gauges; an inertial measurement unit 114 including an accelerometer, a gyroscope, a magnetometer; a magnetic encoder 110; and/or other sensors). The inertial measurement unit 114 can detect user interactions with the controller 102 including translation, rotation, and orientation of the controller and communicate the user interaction via an I2C connection 150 to the SoC 120. The controller 102 can provide controller data associated with the one or more sensors to the virtual surgical simulation code 124 via the communication path 112.

The virtual surgical simulation code 124 can process the image data and the controller data to determine a user interaction with the controller within the field of view of the imaging system 128. In some embodiments, virtual surgical simulation code 124 can include a position tracker that can determine a position and orientation of the controller 102 in a coordinate system associated with the field of view of the imaging system 128. In some embodiments, the coordinate system associated with the field of view can correspond to and/or be used as a coordinate system for the workspace. The position tracker can store the position and orientation of the controller 102 with the simulation data 125. In some embodiments, the image data, the controller data, and historical position and orientation data of the controller 102 can be used to determine a trajectory of the controller 102. The trajectory of the controller can be predicted by the position tracker. The trajectory of the controller can be used by the virtual surgical simulation code 124 to predict the impact on the virtual surgical simulation if the user continues a current interaction with the controller 102. In some embodiments, the virtual surgical simulation code 124 can transmit an alert to the user of the impact associated with continuing an interaction with the controller. For example, the virtual surgical simulation code 124 can generate and transmit an alert the user that continuing the interaction may cause the controller to move to a position outside the workspace.

The mobile device 122 can transmit instructions generated by the virtual surgical simulation code 124 that cause the controller to provide feedback to the user. In response to instructions generated by the virtual surgical simulation code 124, the SoC 120 can cause controller 102 to provide feedback to a user using a second PWM signal 144 to a motor driver 106. The second PWM signal 144 can cause the motor driver 106 to provide a current to the gripper motor 104 and/or the vibration motor 108. In some embodiments, the second PWM signal 144 can be provided in response to instructions generated by the virtual surgical simulation code 124 on the mobile device 122. The magnetic encoder 110 can detect motion of the gripper and transmit one or more pulses 148 to the SoC 120. Each pulse can be associated with a particular angular rotation of the gripper.

In some embodiments, the transformation data structure can include rules to transform the position and orientation of the controller 102 in the coordinate system associated with the field of view of the imaging system 128 to a second coordinate system associated with a 3D virtual environment generated by the virtual surgical simulation code 124. In some embodiments, the portable interaction system 100 can output a representation of the virtual surgical simulation to the display 126. In some embodiments, the representation can be the 3D virtual environment. The representation can include user interface that can be output to the display 126 of the mobile device 122 and/or transmitted to a peripheral screen and/or device. In other embodiments, the 3D virtual environment can be output to an augmented reality headset or a virtual reality headset coupled to the mobile device 122.

In some embodiments, the virtual surgical simulation code 124 can include a training structure module. The training structure module can generate virtual objects associated with various structures for a surgical procedure and/or surgical training tasks modeled by the virtual surgical simulation code 124. The virtual surgical simulation code 124 can include virtual objects for training structures such as pegs and pins for generic dexterity training or anatomical structures for specific surgical procedure dexterity training. In some embodiments, the virtual surgical simulation code 124 can determine an interaction by the user with the controller results in a collision between the virtualized surgical tool and another virtual object.

The virtual surgical simulation code 124 can include feedback instructions that can trigger outputting feedback stimuli at the controller based on an actual or expected collision between the virtualized surgical tool and another virtual object. In some embodiments, the feedback is provided to stimulate different forces imparted on the virtualized tool (e.g., in response to a contact between the virtualized tool and a part of a virtualized patient). In some embodiments, the feedback is provided to indicate whether a virtual action corresponds to a target action (e.g., by providing a vibration or visual indicator in response to detecting a mismatch). The feedback can include kinesthetic, tactile, visual, auditory, and the like. The virtual surgical simulation code 124 can generate data that includes one or more commands and transmit the data via communication path 112. The data can cause the imaging system 128, controller 102, and/or the display 126 to present feedback to the user.

In some embodiments, the feedback can include one or more scores. The virtual surgical simulation code 124 can determine an interaction score based on a target interaction and the virtualized surgical tool interaction with a virtual object such, such as a virtualized anatomical structure or a virtualized training structure. The target interaction can be associated with a particular biological effect in the virtual surgical simulation. The simulation data 125 can include a database of reference virtual surgical simulations. Each reference virtual surgical simulation can include a collection of target interactions necessary to perform a procedure. In some embodiments, one or more target interactions may be associated with a plurality of surgical procedures. For example, a target interaction may include one or more steps to form a surgical knot. The steps to form the surgical knot may be used in a plurality of procedures. In some embodiments, the target interaction can be based on data from surgical simulations completed by expert surgeons.

For example, target interactions for a carpal tunnel release surgery may be accessed in the simulation data 125 and used to determine an interaction score. For this procedure, an example target interaction can be to cut a specific ligament to release a median nerve. In this example, a target biological effect is releasing the median nerve. One or more anatomical structures associated with the surgical procedure can be modeled using virtual objects by the virtual surgical simulation code 124. The interaction score can be based on whether the user's interaction's with the controller transformed to manipulations of the virtualized surgical tool that caused the virtual objects to release the median nerve modeled by the virtual surgical simulation code 124. The interaction score can be based on at least one of a dexterity measurement, an economy of movement measurement, and a motion related measurement. In some embodiments, the 3D virtual environment and the interaction score can be output to the display 126.

Figure 2:
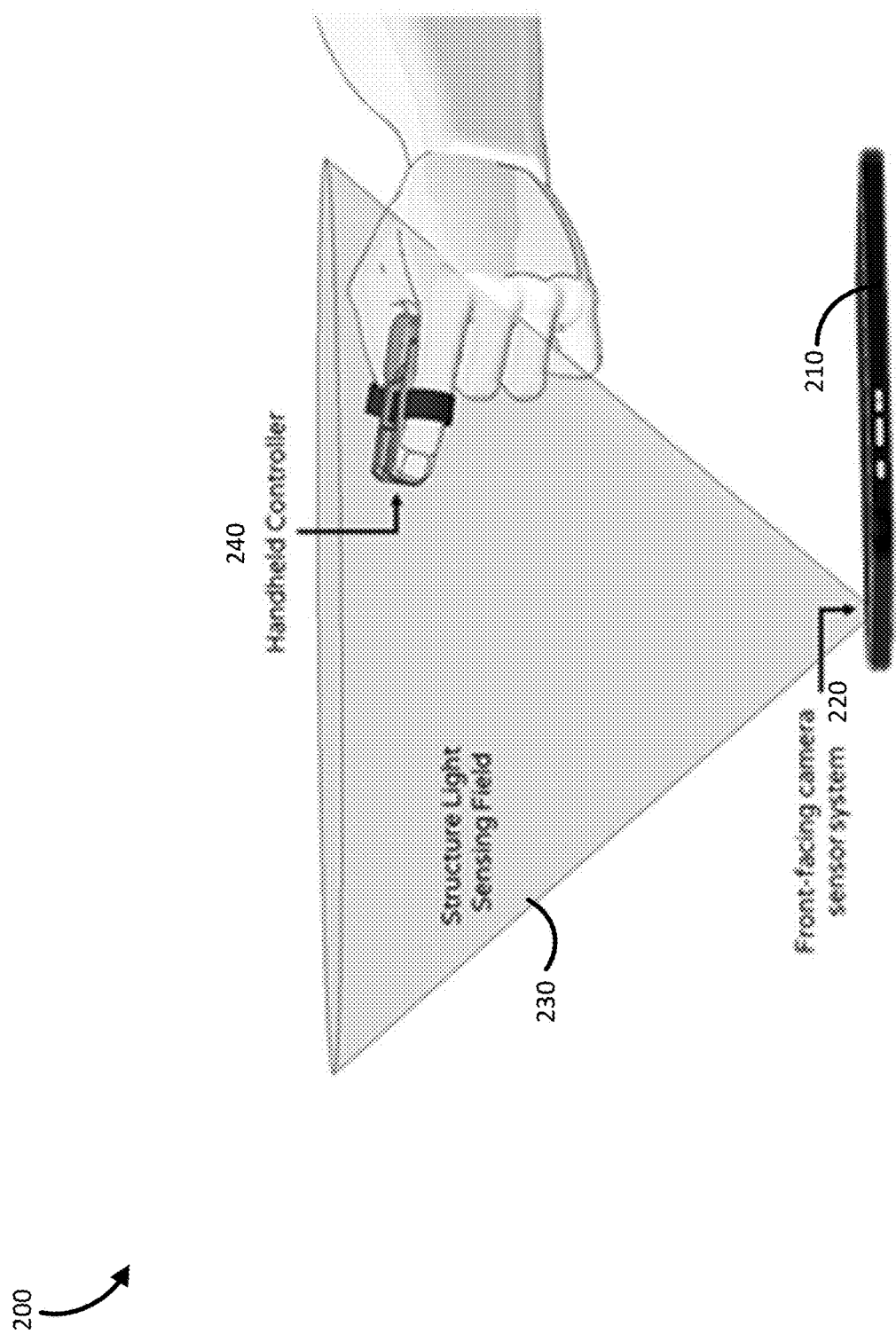
FIG. 2 shows a portable interaction system 200 in accordance with some embodiments of the invention.

FIG. 2 shows an embodiment of a portable interaction system 200. The portable interaction system 200 can include mobile device 210. The mobile device 210 can include instructions to execute the virtual surgical simulation code of the interaction system described in FIG. 1. The mobile device can include an imaging system 220 with a front-facing camera sensor system that the virtual surgical simulation code can control to collect and process image data. A field of view 230 corresponds to the observable area in which the imaging system can detect a user's interaction with a controller 240. The field of view 230 can define a workspace in which a user's interactions with the controller 240 can be observed. The imaging system 220 can include one or more light sensing devices.

Image data can be video data and/or photographic data. The image data can be associated with visible light and/or infrared light.

In some embodiments, the imaging system 220 can include a structured light camera system. The structured light camera system can include an illuminator that projects a light pattern in the field of view 230 of the imaging system 220. The light pattern can include a point cloud, a random pattern, a stripe pattern, etc. The imaging system can collect image data with a reflection of the light pattern superimposed on an image of a scene captured by the front facing camera system. The light pattern can include distortions caused by variations in depth of objects in the field of view 230. In some embodiments, the illuminator projects a light pattern using infrared light.

Figure 5:
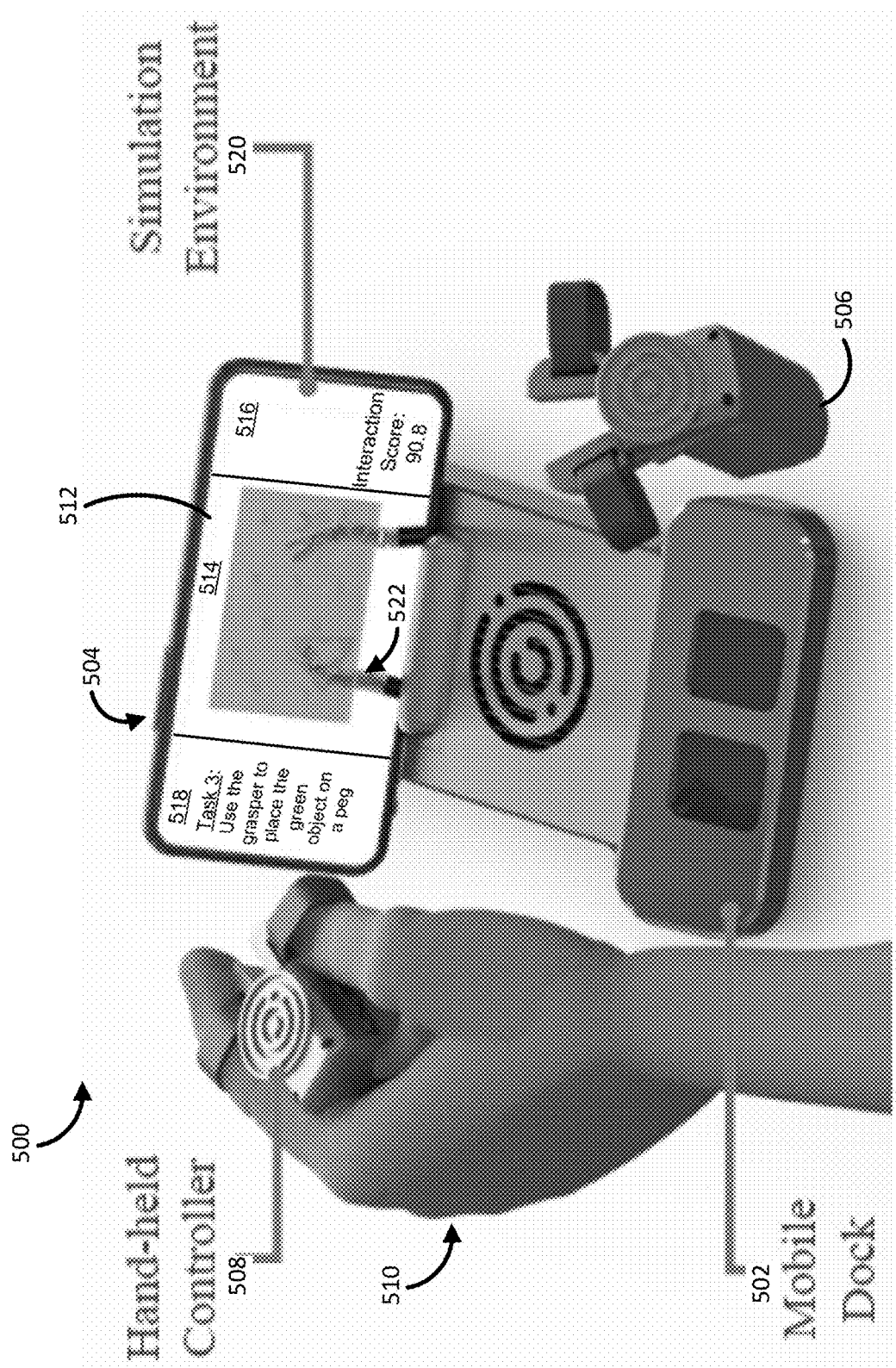
FIG. 5 shows a perspective view of a portable interaction system 500 in accordance with some embodiments of the invention.

The image data associated with a structured light camera system can be processed by the virtual surgery simulation code to detect the distortions in the light pattern projected by the illuminator. In some embodiments, the image data can indicate a shape of an object in the field of view, a shape of the distortion of the light pattern, and/or a magnitude of the distortion in the light pattern that can be used by virtual surgery simulation code to identify a position and/or orientation of the controller 240. The virtual surgical simulation code on the mobile device 210 can generate a 3D position of the controller 240 based on the image data. In some embodiments, the distortions in the light pattern can be converted to a coordinate system associated with the field of view 230. The 3D position can be defined by the coordinate system associated the field of view 230. In some embodiments, a peripheral device can be coupled to the mobile device 210 and transmit image data to the mobile device 210. In some embodiments, a mobile dock, as shown in FIG. 5, can include an additional imaging system.

In some embodiments, electromagnetic data can be processed to track the controller 240. For example, mobile device 210 can include a magnetometer. Movement of the controller 240 near the mobile device 210 can cause fluctuations in the magnetic field detected by the magnetometer. The virtual surgical simulation code can process the magnetic field data generated by the magnetometer to determine the location of the controller 240. In some embodiments, a peripheral device with electromagnetic tracking sensors may be coupled with the mobile device 210 to collect electromagnetic data for determining the position of the controller 240. The controller 240 can emit an electromagnetic signal to assist with tracking and position determination. In some embodiments, the electromagnetic data can be used if the line-of-sight to a controller is obstructed and/or to supplement image data.

Figure 3:
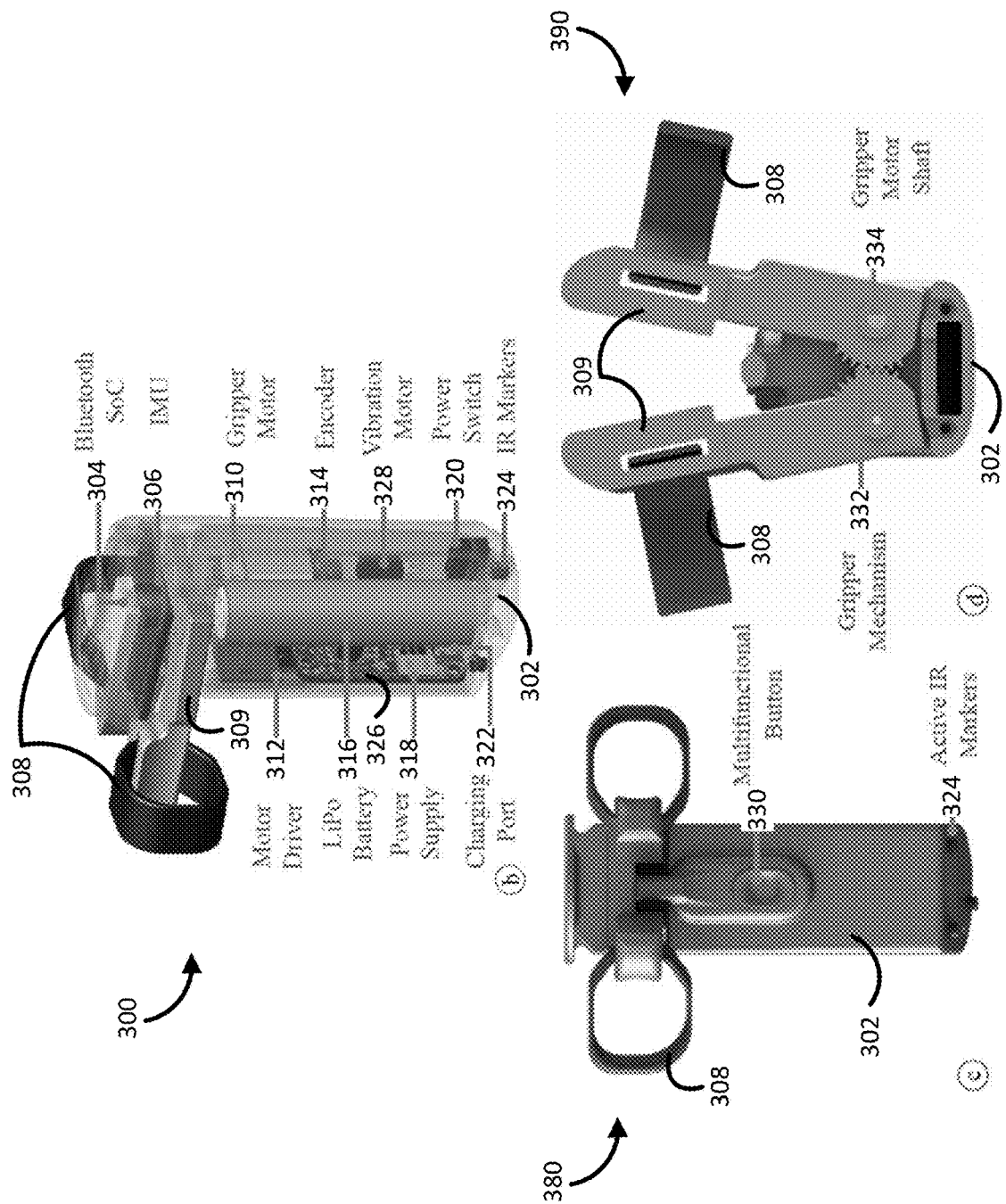
FIG. 3 shows a perspective view 300, an elevation view 380, and a plan view 390 of a controller 302 for use with a portable interaction system in accordance with some embodiments of the invention.

FIG. 3 shows a perspective view 300, an elevation view 380, and a plan view 390 of a controller 302 for use with a portable interaction system. The controller can include an communications unit 304, an inertial measurement unit 306, a gripper 308, a gripper motor 310, a motor driver 312, an encoder 314, a battery 316, a power supply 318, a power switch 320, a charging port 322, one or more IR markers 324, an embedded computer 326, a vibration motor 328, a multifunctional button 330, a gripper mechanism 332, and a gripper motor shaft 334.

The communication unit 304 can be configured for wired or wireless transmission of data to and from the controller 302 (e.g., Bluetooth, Wi-Fi, USB, Ethernet, serial, infrared, etc.) to another device (e.g., a second controller, a mobile device, and/or a mobile dock). The inertial measurement unit 306 can include one or more sensors to detect motion of the controller in space. The one or more sensors in the inertial measurement unit 306 can include accelerometers, gyroscopes, and/or magnetometers. The accelerometer can measure acceleration of the controller along three perpendicular axes (x, y, z). The gyroscope can measure the angular motion of the controller about the three axes (yaw, pitch, roll). The magnetometer can detect the earth's magnetic field or a magnetic field generated for use with the interaction system. The magnetic field can be used to determine the magnetic direction of the controller 302. In some embodiments, the magnetic direction can be transformed to a position (x, y, z) and/or an orientation (yaw, pitch, roll). The inertial measurement unit 306 can provide electronic data to the communication unit 304 for communication of controller data that indicates motion and orientation of the controller 302. In some embodiments, the one or more sensors can be combined in a single package.

The inertial measurement unit 306 can include a processor that processes raw sensor data to generate controller data that indicates a position, orientation, and/or movement of the controller in association with a coordinate system. The virtual surgical simulation code can transform the controller data into a virtual tool manipulation. The virtual tool manipulation can indicate a change relative to one or more of a set of degrees of freedom (e.g., seven degrees of freedom) associated with the virtualized tool. The controller data can be transformed to translation of the virtual tool along three perpendicular axes (x, y, z); rotation about the three axes (yaw, pitch, and roll), and a pinching movement. In some embodiments, the virtual surgical simulation code can include one or more components, such as a position tracker, to transform user interactions with the controller to manipulations of the virtual tool in the virtual surgical simulation.

The controller 302 can include one or more components to detect the pinching movement. In some embodiments, the controller 302 can include fingertip components for the gripper 308 coupled to gripper arms 309 that can be used to interact with controller 302. The gripper arms 309 can include a gripper mechanism 332 and a gripper motor shaft 334 coupled to the gripper motor 310. The gripper motor can be controlled by the embedded computer 326, the encoder 314, and the motor driver 312. The encoder 314 can provide a rotation angle measurement associated with the gripper arms 309. In some embodiments, the controller can include a multifunctional button 330. The multifunctional button 330 can detect user interaction with the controller 302. In some embodiments, the multifunctional button 330 can act as a "clutch" between the controller and the virtual surgical tool. If the multifunction button 330 is functioning as a "clutch" and is engaged, interactions with the controller are not transformed to manipulations of the surgical tool in the virtual surgical simulation.

In some embodiments, the gripper motor 310 and/or the vibration motor 328 can provide haptic feedback to a user. The gripper motor 310 can provide haptic feedback including kinesthetic and tactile feedback to a user via the gripper arms 309. The haptic feedback provided by the gripper arms 309 can indicate manipulation of grasped objects in the virtual surgical simulation to a user. The vibration motor 328 can be coupled to main body of the controller to provide tactile feedback to a user. The haptic feedback can be based on user interaction with the controller and/or instructions generated by the virtual surgical simulation code based on the manipulation of the virtualized surgical tool causing a collision with training and/or anatomical structures.

The controller 302 can include additional sensors such as strain gauge sensors and optical pressure sensors. The strain gauge sensors can convert changes in mechanical force on the gripper arms 309 and/or the multifunctional button 330 into changes in a voltage which can be detected by the embedded computer 326. The embedded computer 326 can process the detected voltages to estimate the tensile and compressive strain applied to the gripper arms 309 and/or the multifunctional button 330. In some embodiments, an optical pressure sensor can be coupled to the gripper arms 309 and/or the multifunctional button 330 to detect user interaction with the controller 302.

The embedded computer 326 can send and/or receive data with the components of the controller 302. In some embodiments, the embedded computer 326 can transmit instructions that cause the components of the controller to perform an associated function. The controller 302 can be powered by a battery 316. The battery can be coupled to the power switch 320, the power supply 318, and the charging port 322. The power supply 318 can provide power to the embedded computer 326 and the various controller 302 components. In some embodiments, the controller 302 can be tethered to a mobile device or mobile dock. The tether can provide a mechanical connection, a data connection and/or a power connection.

The communication unit 304 can be configured for wired or wireless transmission of data to and from the controller 302 (e.g., Bluetooth™, Wi-Fi, USB, Ethernet, serial, infrared, etc.) to another device (e.g., a second controller, a mobile device, and/or a mobile dock). The inertial measurement unit 306 can include one or more sensors to detect motion of the controller in space. The one or more sensors in the inertial measurement unit 306 can include accelerometers, gyroscopes, and/or magnetometers. The accelerometer can measure acceleration of the controller along three perpendicular axes (x, y, z). The gyroscope can measure the angular motion of the controller about the three axes (yaw, pitch, roll). The magnetometer can detect the earth's magnetic field or a magnetic field generated for use with the interaction system. The magnetic field can be used to determine the magnetic direction of the controller 302. In some embodiments, the magnetic direction can be transformed to a position (x, y, z) and/or an orientation (yaw, pitch, roll). The inertial measurement unit 306 can provide electronic data to the communication unit 304 for communication of controller data that indicates motion and orientation of the controller 302. In some embodiments, the one or more sensors can be combined in a single package.

Figure 4:
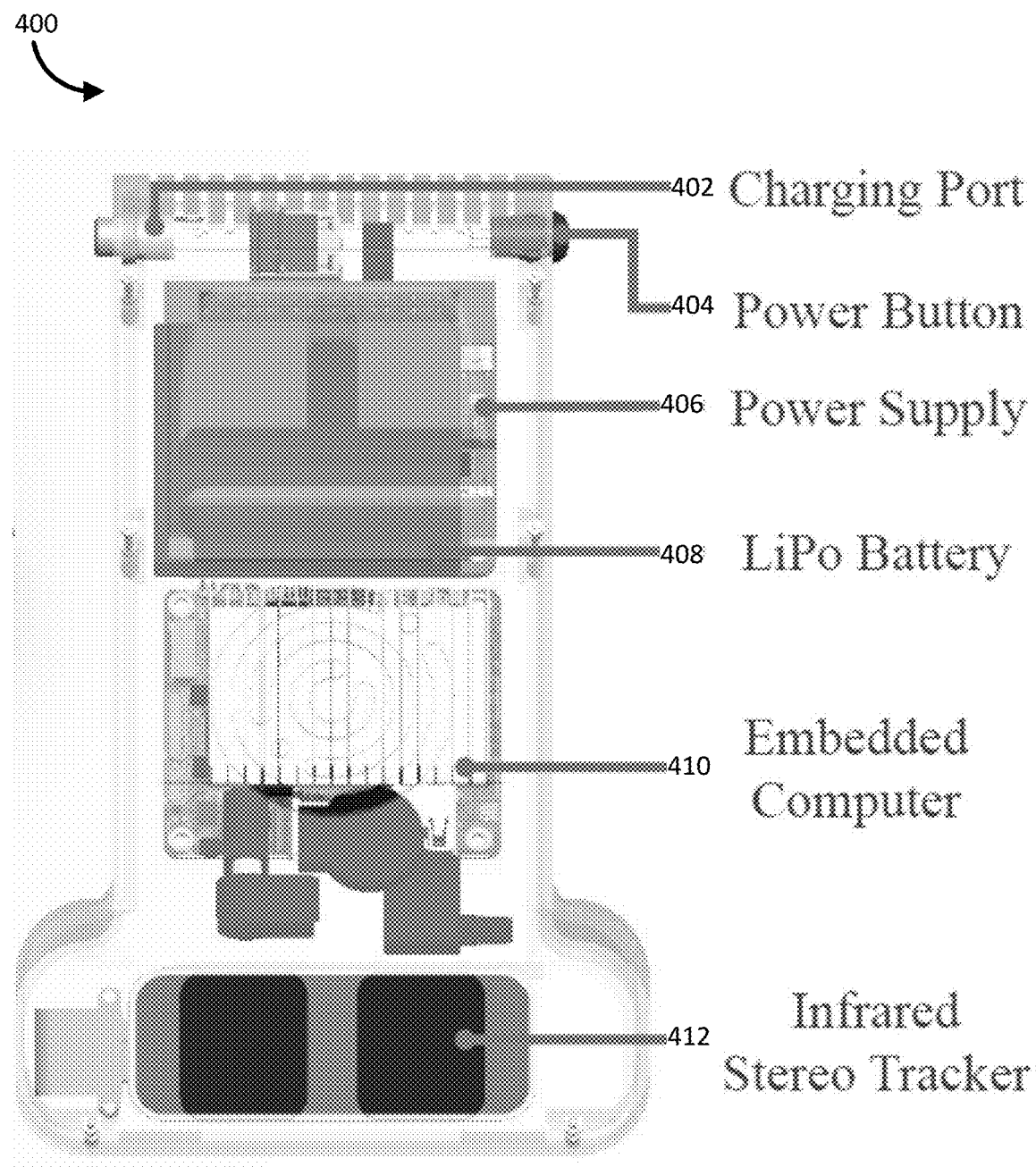
FIG. 4 shows a shows a plan view of a mobile dock 400 that can receive a mobile device controlling the portable interaction system in accordance with some embodiments of the invention.

FIG. 4 shows a plan view of a mobile dock 400 that can receive a mobile device controlling the portable interaction system. In some embodiments, an interaction system can include one or more controllers, a mobile device, and the mobile dock 400. The mobile dock 400 can include a charging port 402, a power button 404, a battery 408, an embedded computer 410, and an infrared stereo tracker 412. The charging port 402 can provide an interface to receive current to charge the mobile dock 400 and, in some embodiments, the mobile device and the one or more controllers of the portable interaction system. The mobile dock 400 can include a battery 408 to improve the portability of the interaction system. An external AC/DC power adapter can be used simultaneously to power the mobile dock 400 while charging the battery 408. The power button 404 can be coupled to the power supply 406. The mobile dock 400 can use the embedded computer 410 to send and receive data and instructions to and from at least one of the infrared stereo tracker 412, one or more controllers, and a mobile device coupled to the mobile dock 400. The mobile device can communicate electronic data with the mobile dock via a wired and/or wireless interface.

The infrared stereo tracker 412 can include an infrared stereo camera. The infrared stereo camera can include two or more image capture devices. Each image capture device in the infrared stereo camera can be equipped with a fisheye lens to capture wide-angle images. The infrared stereo tracker 412 can provide image data that can be used to track the position of the hand-held controller with three degrees of freedom (x, y, z) in a field of view associated with the infrared stereo tracker 412. The field of view of the infrared stereo tracker 412 can form the workspace for the interaction system. In some embodiments, the field of view of the infrared stereo tracker 412 can be combined with the field of view of the mobile device to expand the workspace. The infrared stereo tracker 412 can be positioned in the front of a mobile dock to provide a workspace in front of the mobile device running the virtual surgical simulation code. The infrared stereo tracker 412 can include an LED for illumination of the field of view. In embodiments with a controller that includes active infrared markers, an LED that is integrated in the infrared stereo tracker 412 can be disabled as the active infrared markers can be detected by the infrared stereo tracker 412. The infrared stereo tracker 412 can be coupled to the embedded computer 410. In some embodiments, the infrared stereo tracker 412 is connected through a USB 3.0 connection to the embedded computer 426.

The embedded computer 426 can receive and process image data that includes a stereo pair of images captured by the infrared stereo tracker 412. In some embodiments, the image data captured by the infrared stereo tracker 412 can include grayscale images in the infrared spectrum. In some embodiments, the infrared stereo tracker 412 can capture frames at a rate of 64 stereo frames per second. In some embodiments, the embedded computer 426 can process the image data and calculate the position of each controller in the workspace. To perform 3D tracking, first, distortion in a grayscale camera image associated with the fisheye lens can be reduced using a built-in distortion map. The distortion built-in distortion map can be used to transform the grayscale camera image associated with the fisheye lens to the coordinate system associated with the workspace. Next, to simplify identification of the controller, the grayscale camera image can be thresholded to binary pixel values to segment the infrared markers. In some embodiments, the marker positions can be identified using an algorithm, for example, the SimpleBlobDetector algorithm from OpenCV. In some embodiments, image data associated with the stereo pair of images can be transmitted to the mobile device running the virtual surgical simulation. The embedded computer 426 and/or the mobile device can detect the infrared markers using the thresholding algorithm and triangulating their 3D position using the calibrated cameras.

In some embodiments, more than one controller can be used in the workspace. In embodiments with more than one controller, various controllers (e.g., left and right hand controllers) can be distinguished by the relative position of each marker. The leftmost detected marker can be recognized as the left controller and vice versa. Further, pairs of corresponding markers in the stereo images can be triangulated using stereo parameters determined during a calibration mode. In some embodiments, the stereo parameters can be determined during the calibration mode with a chessboard pattern. The triangulated points in the workspace can be smoothened over time using a moving average filter. The position tracking and prediction can be performed using an extended Kalman filter to improve the robustness of the tracking in events of temporary occlusion.

In some embodiments, a 3D position of the controller can be determined using a coordinate system associated with the field of view of the infrared stereo tracker 412. The coordinate system of the field of view can correspond to the coordinate system of the workspace. The embedded computer 426 can receive controller data via a wired and/or wireless connection. The mobile dock 400 can receive quaternion orientation data from the one or more controllers. After processing the image data from the infrared stereo tracker 412 and determining the position of the controller using the image data and the controller data, the embedded computer 426 can transmit a combined 6-degree of freedom pose of the controllers through the wired and/or wireless connection to the mobile device. The 6-degree of freedom pose can include position (x, y, z) data and orientation (yaw, pitch, roll) data. In some embodiments, the position data and orientation data can be based on the image data and quaternion orientation data. In some embodiments, a Wi-Fi connection can be established through a local network that the embedded computer 426 creates. In some embodiments, a wireless function can include a battery powered system integrated in the mobile dock 400.

The infrared stereo tracker 412 can provide image data to the mobile device and the virtual surgical simulation code of the portable interaction system. The infrared stereo tracker 412 can emit infrared light and receive reflected infrared light in the form of image data. In some embodiments, a first field of view associated with the infrared stereo tracker 412 and a second field of view associated with the mobile device can overlap. The overlapping fields of view can form a workspace in which to use a controller for the portable interaction system.

FIG. 5 shows a perspective view of a portable interaction system 500. The portable interaction system 500 includes a mobile dock 502, a mobile device 504, a first handheld controller 506 and a second handheld controller 508. A user's hand 510 is also shown interacting with the second handheld controller 508. The mobile device 504 includes a display 512. The display 512 shown in FIG. 5 is outputting a representation of the virtual surgical simulation 520. The representation can be subdivided into a 3D virtual environment display 514, an interaction score display 516, and a step-by-step guidance display 518. In some embodiments, the display 512 may not be subdivided and, for example, the 3D virtual environment display 514 may use the entire display 512. In embodiments with a single display, the virtual surgical simulation may detect a stage of the simulation and display a task or an interaction score in response to the stage of the simulation.

In some embodiments, the user interface may present a user with an identification of each of a plurality of virtual surgical tool models (e.g., by displaying a representation of each corresponding virtualized tool). The user may enter a selection using display 512 if it is touch enabled or by interacting with one of the controllers. A profile associated with the selected model can then be used to translate interactions with the controller 508 into interactions with a virtualized tool 522. The tool profile can include dimensions, shapes, axes of rotation, tensions, movement constraints, etc. associated with a surgical tool. The virtualized tool 522 can correspond to, for example, a pair of graspers, diathermy, scissors, etc.

The virtual surgical simulation code can update the 3D virtual environment display 514 to represent the virtualized interaction with the virtualized tool 522. The 3D virtual environment display 514 can be generated using a physics engine that generates virtual objects and detects collisions between the virtual objects. The virtualized tool 522 can be modeled by the virtual surgical code using rigid body segments connected via hinge joints. In some embodiments, the joint angles can be stabilized by applying an angular torque via a proportional controller for the joint angle's error at each joint to achieve desired joint angles. The same approach can be used to match the simulated gripping angle with the measured angle read via the first controller 506 or the second controller 508. In some embodiments, an arm locking mechanism can lock the virtualized surgical tool at a position of interest in the 3D virtual environment and limit lateral movement of the virtualized surgical tool during surgery.

In some embodiments, the virtual surgical simulation may detect an object in addition to the first controller 506 and the second controller 508 in the image data. The virtual surgical simulation may determine the object in the image data is a hand 510 of the user. In some embodiments, the virtual surgical simulation may determine and store hand features associated with the hand 510 of the user. Hand features can include size and volume data, finger and joint position data, angles of rotation associated features, etc. The hand features can be used to update the one or more transformation rules associated with the virtual surgical simulation. The hand features can be used to determine target hand features associated with a surgical procedure. As a user progresses through a surgery, the virtual surgical simulation may provide feedback to a user when a target hand feature is not compatible with an upcoming manipulation of the virtual surgical tool. For example, the virtual surgical simulation may estimate an available degrees of rotation based on target hand features. The virtual surgical simulation may determine that the available degrees of rotation is less than a required rotation angle associated with completing the manipulation of the virtual surgical tool for a particular task. In response, the virtual surgical simulation can provide an alert to the user to use the multifunction button on a controller to reposition the hand to prepare for the particular task. In some embodiments, the virtual surgical simulation can determine a user profile associated with the hand of a specific user. The virtual surgical simulation can access, update, and/or store hand features associated with the user profile.

In some embodiments, the virtual surgical simulation code can determine the first controller 506 or the second controller 508 is associated with the virtualized tool 522, and the surgical tool. A controller may have a unique marker configuration to identify the corresponding surgical tool. One or more transformation rules can be updated based on the tool profile. The feedback provided by the virtual surgical simulation code can be determined based on the virtualized surgical tool, the controller, the tool profile, and the virtual surgical simulation.

Figure 6:
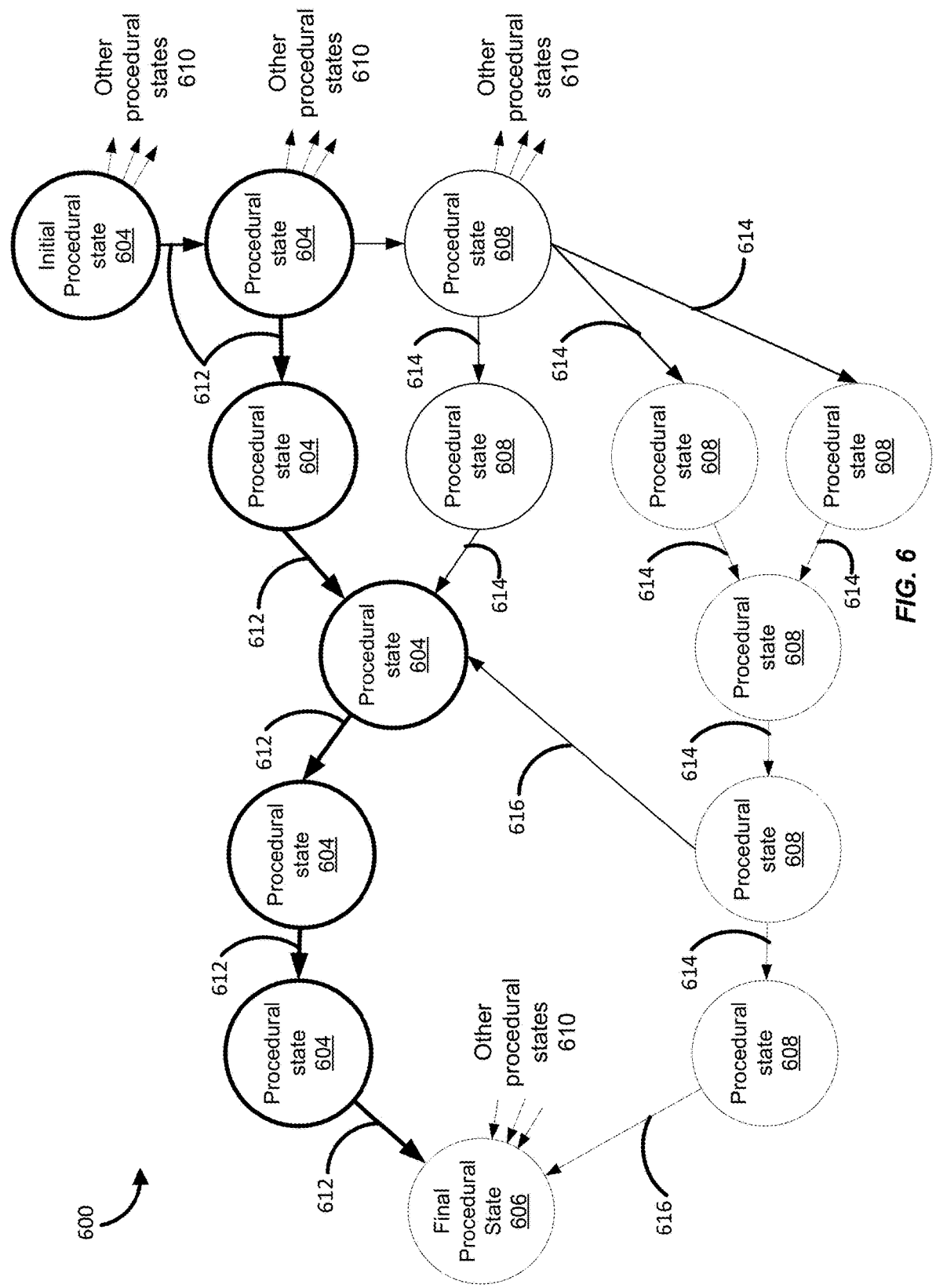
FIG. 6 shows a model 600 of a surgical procedure or a training task in accordance with some embodiments of the invention.

FIG. 6 shows model 600 of a surgical procedure or a training task. The model can be associated with a map representing an ordered progression of procedural states in a type of surgical procedure. More specifically, each node represents a procedural state. Each inter-node connection can indicate how the states may change during the procedure and can correspond to one or more surgical actions that can cause the simulated procedure to transition between multiple states. The model can be accessed when the user begins the virtual surgical simulation or selects a new state or procedure from a user interface. The user interface can also indicate training progression through the model 600. The surgical procedure can be represented by a plurality of nodes and be interconnected by a plurality of edges. The actions can be associated with a manipulation of a surgical tool. In some instances, the model indicates preferred or target partial or full trajectories between the states (e.g., as represented by the bolded nodes in FIG. 6). For example, a full target trajectory may be identified as a path across nodes from a node representing an initial procedural state to another node representing a target procedural state (represented by a final node 606). As another example, at each node, a preferred next node can be indicated.

The transition from a current node to a next node may be determined by an interaction score, patient characteristics, user input, and, in some cases, chance. In some embodiments, the edges can be associated with a chance variable that is used to determine the next node presented to a user of an interaction system. The chance variable may be representative of a weighted probability of transitioning from a current node to a next node from a plurality of other nodes. In some embodiments, a non-preferred edge 614 may cause the user to transition to a non-preferred node 608. In some cases, a surgical procedure may include one or more edges 616 that are associated with actions that cause the procedural state to transfer from a non-preferred procedural state to a preferred procedural state. In some embodiments, the surgical graph may be a global surgical graph and each node may include edges associated with a variety of other procedural states 610 that a patient my transition to during a surgery.

Using the model 600 associated with a type of surgical procedure, the virtual surgical simulation code can include a model for a virtualized surgical tool to be represented in the virtual surgical simulation based on the surgical procedure. The virtual surgical simulation code can determine a manipulation associated with the virtualized surgical tool and causes a transition from a current node in the map to a new node in the map. After transitioning, the virtualized surgical simulation code can update the virtual surgical simulation based on the new node.

In another embodiment, the nodes can be assigned weighted probabilities. For example, the virtual surgical simulation code can access a first node associated with a first weighted probability and a second node associated with a second weighted probability. The virtual surgical simulation code can determine a target manipulation associated with the first node and the second node. In some instances, the target manipulation is indicated by a first edge connecting the current node to the first node and a second edge connecting the current node to the second node. The virtual surgical simulation code can determine a target score using the target manipulation and the manipulation associated with the virtualized surgical tool and select the new node based on the first weighted probability, the second weighed probability, and the target score. In some embodiments, the target manipulation is based on data associated with trained surgeons.

Figure 7:
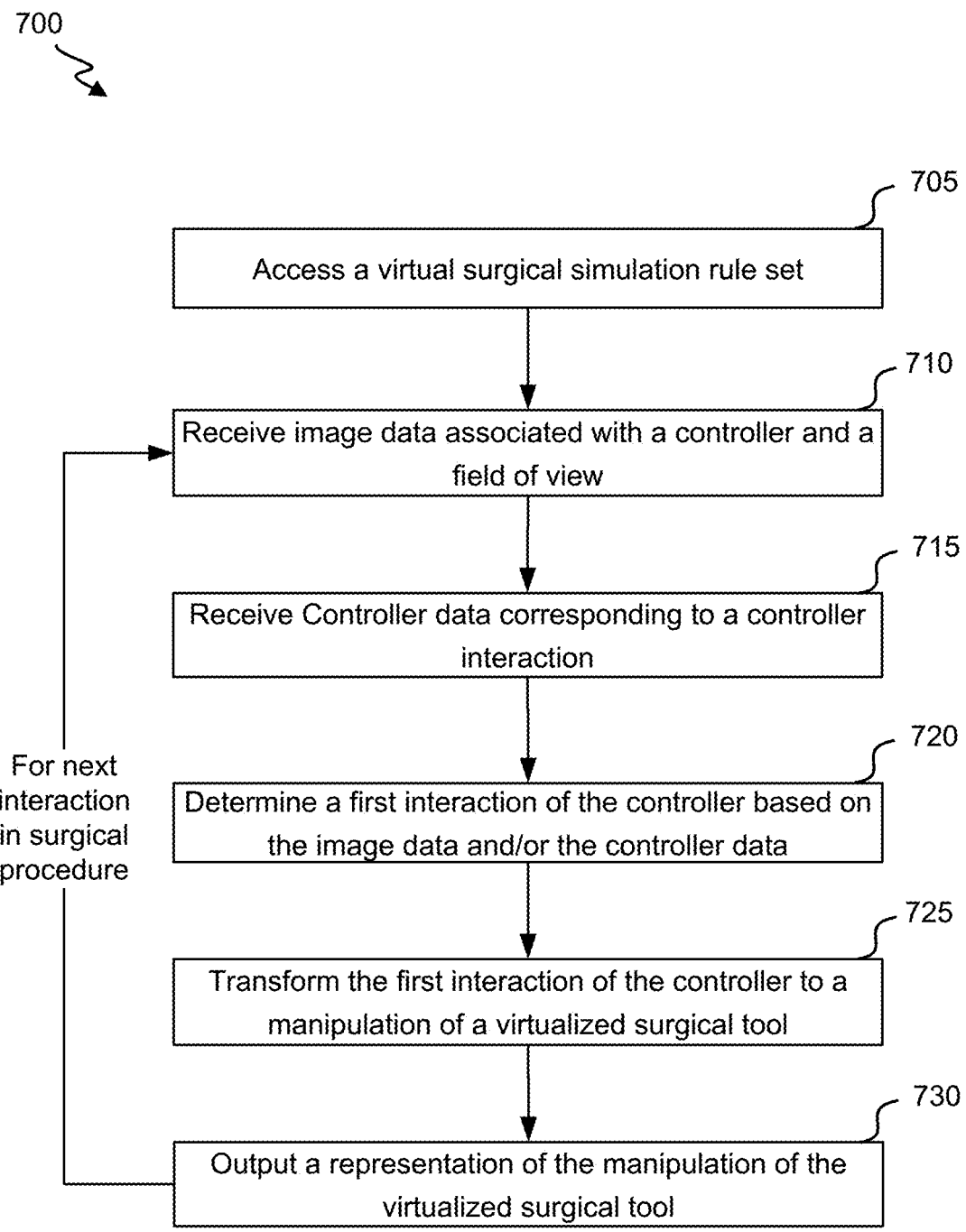
FIG. 7 shows a flowchart of a process 700 for updating a dexterity training system in accordance with some embodiments of the invention.

FIG. 7 shows a flowchart of a process 700 for updating a dexterity training system.

Process 700 begins at block 705 where a virtual surgical simulation rule set is accessed. The virtual surgical simulation rule set can be associated with a type of surgical procedure. The type of surgical procedure can be as simple as a pick and place task or a complex type of surgical procedure with multiple steps such as a knee replacement surgery. In some embodiments, the virtual surgical simulation can include one or more models representing training and/or anatomical structures, a position tracker, a model for a virtualized surgical tool, a 3D virtual environment, a feedback component, and a set of one or more transformation rules that correspond to manipulating the model for the virtualized surgical tool in the 3D virtual environment in the virtual surgical simulation.

At block 710, image data associated with a controller and a workspace is received. The workspace can be associated with a field of view of an imaging system in which a user can interact with the controller of the dexterity training system. The field of view can be associated with an imaging system on a mobile device and/or a mobile dock designed for use with the dexterity training system.

At block 715, controller data corresponding to a controller interaction is received. For example, controller data can include electronic data that represents controller interactions such as a user exerting a force on a gripper and/or a multifunction button on a controller. In some embodiments, controller data associated with a plurality of controllers can be received. The controller data can represent force and/or pressure applied by the user on the controller. In some embodiments, the controller data can include acceleration, orientation, and/or position data to assist with determining controller interactions performed by the user.

At block 720, a first interaction of the controller within the workspace is determined based on at least one of the image data and the controller data. The interaction can include translation of the controller in one or more directions, rotation of the controller, and/or pinching/opening a gripper coupled to the controller. In some embodiments, a first set of coordinates can correspond to the workspace. The interaction of the controller can correspond to translation and/or rotation of the controller in the first set of coordinates.

At block 725, the first interaction of the controller can be transformed to a manipulation of the virtualized surgical tool in the virtual surgical simulation. The manipulation of the virtualized surgical tool can correspond to translation or rotation in the virtual surgical simulation. In some embodiments, the translation or rotation of the virtualized surgical tool be associated with movement in a second set of coordinates that correspond to the virtual surgical simulation. The set of one or more transformation rules can be used to transform the first interaction of the controller from the workspace to the manipulation of the virtualized surgical tool in the virtual surgical simulation.

At block 730, a representation of the manipulation of the virtualized surgical tool can be output to a user interface. In some embodiments, the user interface can be a display on the mobile device with the virtual surgical simulation. In other embodiments, the representation can be output to a peripheral device such as a secondary display and/or a VR/AR headset. After outputting the representation, the process can return to block 710, such that each of blocks 710-730 is performed for each controller interaction performed by a user.

Figure 8:
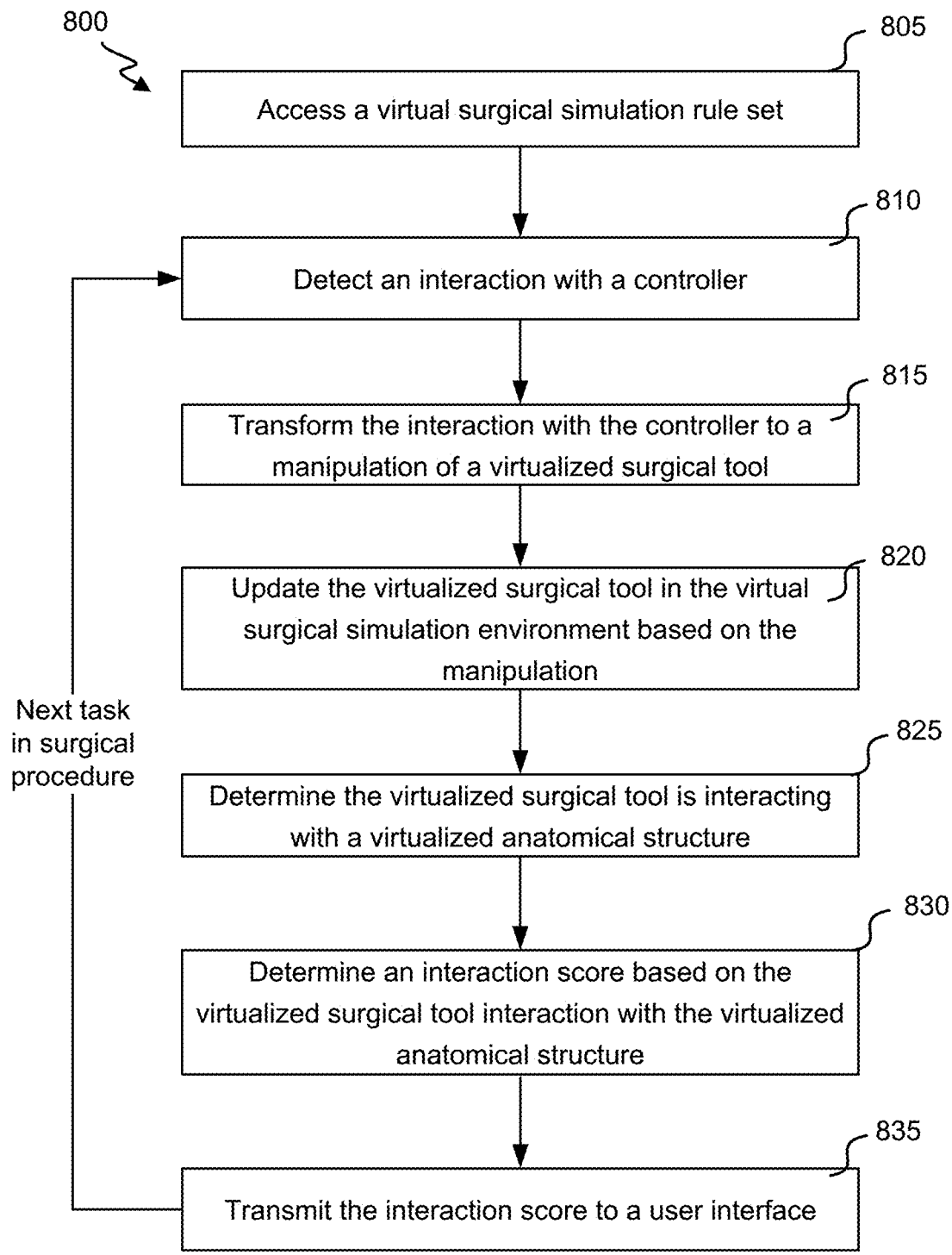
FIG. 8 shows a flowchart of a process 800 for transformations of virtualized surgical tool interactions in accordance with some embodiments of the invention.

FIG. 8 shows a flowchart of a process 800 for transformations of virtualized surgical tool interactions. Process 800 begins at block 805 where a virtual surgical simulation rule set is accessed as described in relation to FIG. 7. At block 810, an interaction with a controller can be detected. The interaction with a controller can be detected from image data associated with a workspace of a dexterity training system and data transmitted by the controller. At block 815, the interaction with the controller can be transformed to a manipulation of a virtualized surgical tool.

At block 820, the virtualized surgical tool in the virtual surgical simulation can be updated based on the manipulation. The virtual surgical simulation can include a position and orientation the virtualized surgical tool. In some embodiments, the virtual surgical tool can be represented by one or more virtual objects in the virtual surgical simulation. The virtual surgical simulation can include and use a physics engine to simulate the physical interactions between one or more virtual objects (e.g., anatomical structures, training structures, virtualized surgical tools).

At block 825, an interaction between the virtualized surgical tool and a virtualized anatomical structure can be determined based on the updated virtualized surgical tool. At block 830, an interaction score based on the virtualized surgical tool interaction with the virtualized anatomical structure can be determined. The interaction score can be determined by comparing the interaction with a target interaction based on a preferred characteristics of the interaction. The preferred characteristics can include, for example, depth of manipulation, speed of manipulation, position of the manipulation, etc. At block 835, the interaction score can be transmitted to a user interface. In some embodiments, the user interface can be a touch screen display on the mobile device with the virtualized surgical simulation. In other embodiments, the interaction score can be transmitted to a peripheral device such as a secondary display, an external memory, and/or a VR/AR headset. After transmitting the interaction score, the process can return to block 810, such that each of blocks 810-835 is performed for each controller interaction performed by a user.

Figure 9:
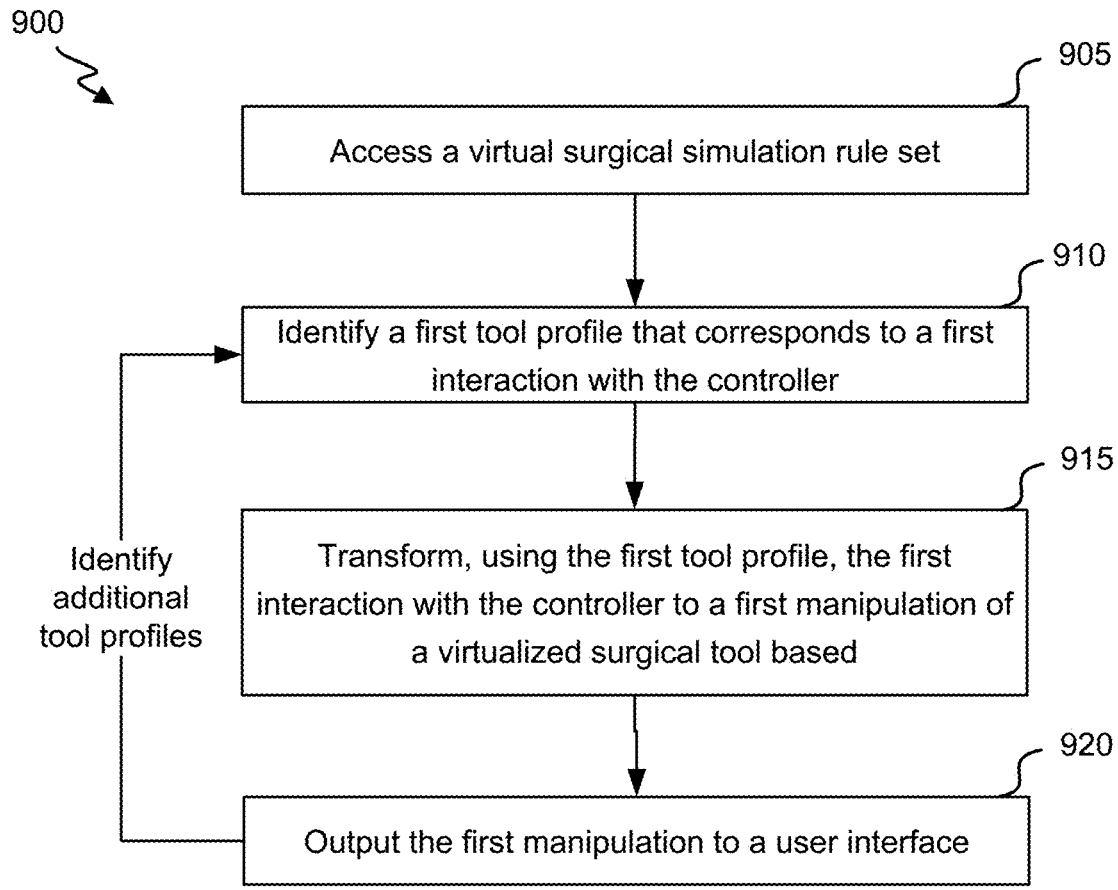
FIG. 9 shows a flowchart of a process 900 of identifying tool profiles associated with a controller of a dexterity training system in accordance with some embodiments of the invention.

FIG. 9 shows a flowchart of a process 900 of identifying tool profiles associated with a controller of a dexterity training system. Process 900 begins at block 905 where a virtual surgical simulation rule set is accessed as described in relation to FIG. 8. In some embodiments, the virtual surgical simulation includes one or more tool profiles and each of the one or more tool profiles can be associated with a unique set of one or more transformation rules. Each of the one or more tool profiles can be associated with a model that corresponds to a virtualized surgical tool to be represented in the virtual surgical simulation.

At block 910, a first tool profile can be identified based on a first interaction with the controller. The first tool profile can be identified from a plurality of tool profiles associated with the virtual surgical simulation. At block 915, the first interaction with the controller can be transformed to a first manipulation of a first virtualized surgical tool. At block 920, the first manipulation can be output to a user interface. After outputting the first manipulation to a user interface, the process can return to block 910, such that each of blocks 910-920 is performed for each tool profile associated with an interaction with a controller.

Figure 10:
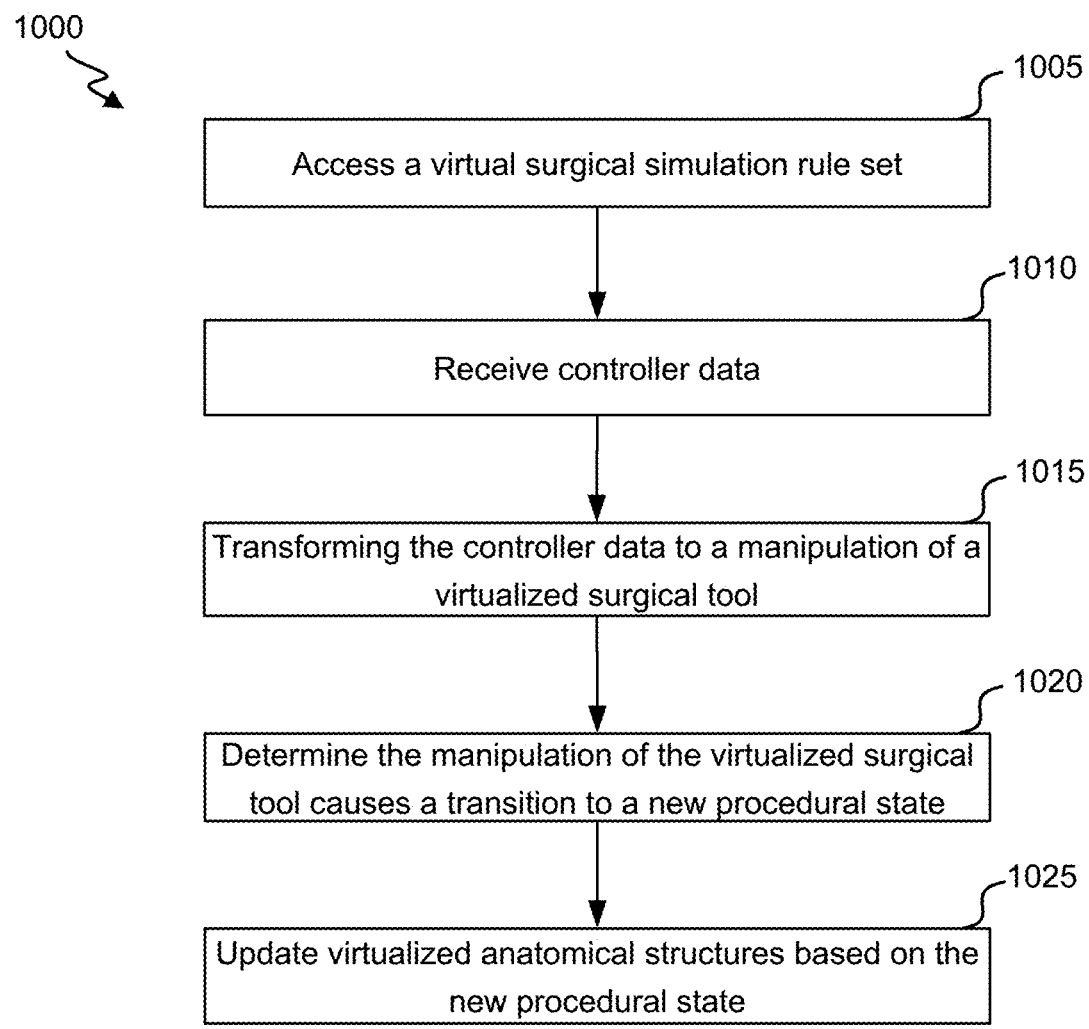
FIG. 10 shows a flowchart of a process 1000 for updating procedural states in a dexterity training system in accordance with some embodiments of the invention.

FIG. 10 shows a flowchart of a process 1000 for updating procedural states in a dexterity training system. Process 1000 begins at block 1005 where a virtual surgical simulation rule set is accessed. The virtual surgical simulation can be associated with a type of surgical procedure. In some embodiments, the type of surgical procedure is associated with a map representing an ordered progression of the type of surgical procedure. The ordered progression can include a plurality of interconnected nodes, each node representing a procedural state. The virtual surgical simulation can include a model for a virtualized surgical tool to be represented in the virtual surgical simulation. The nodes can be interconnected by one or more edges that represent actions that cause a transition from a current procedural state to a next procedural state. The actions can be associated with one or more manipulations of the virtualized surgical tool.

At block 1010, controller data representing an interaction with a controller can be received. At block 1015, the controller data can be transformed to a manipulation of the virtualized surgical tool in the virtual surgical simulation. At block 1020, the manipulation of the virtualized surgical tool can cause a transition to a new procedural state associated with a new node in the map, wherein the new node is interconnected with a current node. At block 1025, one or more virtualized anatomical structures associated with the type of surgical procedure in the virtual surgical simulation can be updated based on the new procedural state.

Figure 11:
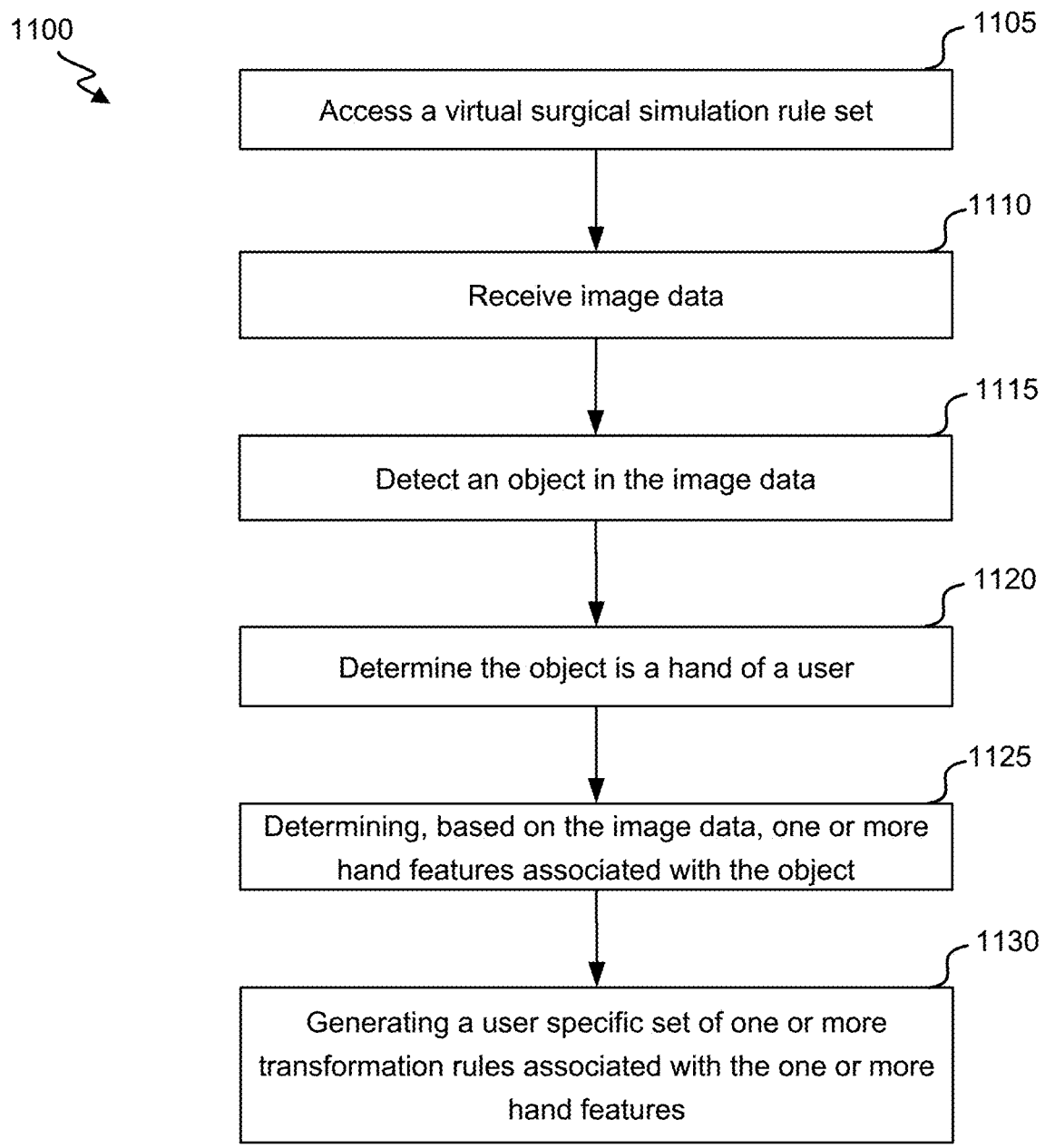
FIG. 11 shows a flowchart of a process 1100 for updating a virtual surgical simulation based on a digital model of a hand in accordance with some embodiments of the invention.

FIG. 11 shows a flowchart of a process 1100 for updating a virtual surgical simulation based on a digital model of a hand. Process 1100 begins at block 1105 where a virtual surgical simulation rule set is accessed. The virtual surgical simulation can include one or more default transformation rules to transform user interactions to virtualized tool manipulations. At block 1110, image data can be received. At block 1115, an object in the image data can be detected. At block 1120, the process can determine the object in the image data is a hand of a user. At block 1125, the process can identify, based on the image data, one or more hand features associated with the object. At block 1130, a user specific set of one or more transformation rules associated with one or more hand features can be generated.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

As used herein, a mobile device can include a device that includes one or more electronic components (e.g., an integrated chip) that can communicate with another device. For example, a mobile device can be a computing device that includes at least one processor coupled to a memory that stores instructions or code for execution by the processor. The mobile device may be a communication device that can be transported and operated by a user. The mobile device may provide remote communication capabilities to a network. The mobile device can be configured to transmit and receive data or communications to and from other devices. A mobile device may be in a form such as a mobile phone (e.g., smart phone, cellular phone, etc.), a tablet, a portable media player, a personal digital assistant device (PDA), a wearable device (e.g., watch, health monitoring device such as a fitness tracker, etc.), electronic reader device, etc. Examples of mobile devices may also include portable computing devices (e.g., laptops, netbooks, ultrabooks, etc.). In some embodiments, a mobile device can include one or more sensors configurable to collect data. The sensors can include a structured light field camera, an infrared camera, a visible light camera, accelerometers, gyroscopes, magnetometers, an IMU, microphones, and the like.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a component, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer implemented method comprising:
accessing a virtual surgical simulation associated with a type of surgical procedure, wherein the virtual surgical simulation includes a set of one or more transformation rules that correspond to a model for a virtualized surgical tool to be represented in the virtual surgical simulation, the virtualized surgical tool being simulated by a controller that is handheld;
receiving image data associated with the controller that is handheld and a workspace, wherein the workspace is associated with a field of view of an imaging system and/or a stereo tracker that captures the image data;
processing the image data to discard the image data without the controller in the field of view;
receiving controller data corresponding to a controller interaction, the controller data being measured by one or more sensors embedded in the controller;
determining a first interaction of the controller that is handheld within the workspace based on at least one of the image data and the controller data;
transforming, using the set of one or more transformation rules, the first interaction of the controller to a manipulation of the virtualized surgical tool in the virtual surgical simulation; and
outputting a representation of the manipulation of the virtualized surgical tool.

2. The method of claim 1 wherein the image data is generated based on projection of a structured light field.

3. The method of claim 1 further comprising projecting a light pattern that is present in the image data.

4. The method of claim 3 further comprising:
detecting a distortion in the light pattern;
determining a shape of an object in the image data based on the distortion in the light pattern; and
determining the shape of the object is the controller.

5. The method of claim 1 wherein receiving image data further comprises:
emitting infrared light; and
receiving, by an infrared stereo camera, the image data.

6. The method of claim 1 wherein the virtualized surgical tool is determined based on receiving a tool model selected by a user.

7. The method of claim 1 wherein the controller data is associated with seven degrees of freedom.

8. The method of claim 1 wherein the controller is tethered to a mobile device.

9. The method of claim 1 wherein determining the manipulation of the virtualized surgical tool further comprises determining a trajectory associated with the controller.

10. The method of claim 1 further comprising detecting one or more markers associated with the controller from the image data.

11. The method of claim 10 further comprising:
determining three or more markers are present in the image data; and
determining, using the three or more markers, a full pose of a rigid body in a workspace coordinate system corresponding to the controller.

12. The method of claim 1 wherein the virtual surgical simulation further comprises a 3D environment.

13. The method of claim 1 wherein the virtual surgical simulation is output to a display on a mobile device.

14. The method of claim 1 wherein the virtual surgical simulation is output to an augmented reality headset.

15. The method of claim 1 wherein the virtual surgical simulation is output to a virtual reality headset.

16. The method of claim 1 further comprising transmitting data to the controller via at least one of a Bluetooth™ connection and a Wi-Fi connection.

17. The method of claim 1 wherein the controller comprises gripper arms with fingertip components and a gripper motor controlled by an embedded computer of the controller, and the controller data further comprises pressure data associated with force sensors on the gripper arms of the controller.

18. The method of claim 1, wherein the set of one or more transformation rules are updated based on one or more hand features of a user.

19. A computer-program product tangibly embodied in a non-transitory machine-readable storage medium, including instructions configured to cause one or more data processors to perform actions including:
accessing a virtual surgical simulation associated with a type of surgical procedure, wherein the virtual surgical simulation includes a set of one or more transformation rules that correspond to a model for a virtualized surgical tool to be represented in the virtual surgical simulation, the virtualized surgical tool being simulated by a controller that is handheld;
receiving image data associated with the controller and a workspace, wherein the workspace is associated with a field of view of an imaging system and/or a stereo tracker that captures the image data;
processing the image data to discard the image data without the controller in the field of view;
receiving controller data corresponding to a controller interaction, the controller data being measured by one or more sensors embedded in the controller;
determining a first interaction of the controller within the workspace based on at least one of the image data and the controller data;
transforming, using the set of one or more transformation rules, the first interaction of the controller to a manipulation of the virtualized surgical tool in the virtual surgical simulation; and
outputting a representation of the manipulation of the virtualized surgical tool.

20. A system comprising:
one or more data processors; and
a non-transitory computer readable storage medium containing instructions which when executed on the one or more data processors, cause the one or more data processors to perform actions including:
accessing a virtual surgical simulation associated with a type of surgical procedure, wherein the virtual surgical simulation includes a set of one or more transformation rules that correspond to a model for a virtualized surgical tool to be represented in the virtual surgical simulation, the virtualized surgical tool being simulated by a controller that is handheld;
receiving image data associated with a controller and a workspace, wherein the workspace is associated with a field of view of an imaging system and/or a stereo tracker that captures the image data;
processing the image data to discard the image data without the controller in the field of view;
receiving controller data corresponding to a controller interaction, the controller data being measured by one or more sensors embedded in the controller, wherein the controller comprises gripper arms with fingertip components and a gripper motor controlled by an embedded computer of the controller, and the controller data further comprises pressure data associated with force sensors on the gripper arms of the controller;
determining a first interaction of the controller within the workspace based on at least one of the image data and the controller data;
transforming, using the set of one or more transformation rules, the first interaction of the controller to a manipulation of the virtualized surgical tool in the virtual surgical simulation, and
outputting a representation of the manipulation of the virtualized surgical tool.

* * * * *